United States Patent [19]

Stetler

[11] Patent Number: 5,576,186
[45] Date of Patent: Nov. 19, 1996

[54] DIAGNOSIS AND MONITORING OF RHEUMATOLOGICAL DISEASES BY DETECTION OF ANTI-EF1-α ANTIBODIES

[75] Inventor: Dean A. Stetler, Lawrence, Kans.

[73] Assignee: The University of Kansas, Lawrence, Kans.

[21] Appl. No.: 299,351

[22] Filed: Sep. 1, 1994

[51] Int. Cl.$^6$ .................. G01N 33/543; G01N 33/564
[52] U.S. Cl. .................. 435/7.92; 435/7.4; 435/7.95; 435/975; 436/506; 436/518; 514/179
[58] Field of Search .................. 435/7.4, 7.92, 435/975, 7.95; 436/506, 518; 514/179

[56] References Cited

U.S. PATENT DOCUMENTS 5,385,824  1/1995  Hoet et al. .................. 435/6

OTHER PUBLICATIONS

Uchiumi et al.; A Human Autoantibody Specific For a Unique Conserved Region of 28 S Ribosomal RNA Inhibits The Interaction of Elongation Factors 1α and 2 with Ribosomes; vol. 266, No. 4, Issue of Feb. 5, pp. 2054–2062, 1991; The Journal of Biological Chemistry.

*Primary Examiner*—David Saunders
*Attorney, Agent, or Firm*—Hovey, Williams, Timmons & Collins

[57]  ABSTRACT

A method and assay kit are provided for diagnosing systemic lupus erythematosus by detecting a concentration of anti-EF-1α antibodies that may be found within a sample of body fluid. The assay employs substantially pure EF-1α antigen, which is preferably bound to a polystyrene support, and an indicator reagent for detecting and quantifying a quantity of anti-EF-1α antibody that attaches to the bound antigen. The support and bound antigen are contacted with the fluid sample to allow the formation of an antigen/antibody complex between the support-bound EF-1α antigen and the anti-EF-1α antibody. The urine-sample assay has a sensitivity for active SLE of at least about 90%, and a specificity of about 90%.

25 Claims, No Drawings

DIAGNOSIS AND MONITORING OF RHEUMATOLOGICAL DISEASES BY DETECTION OF ANTI-EF1-α ANTIBODIES

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The present invention pertains to the field of equipment and methods for diagnosing diseases and, more specifically, to an assay and assay kit that indicate rheumatological diseases such as systemic lupus erythematosus ("SLE"). More particularly, the preferred assay utilizes a solid support having a quantity of EF-1α enzyme bound to the support. The support is then contacted with body fluids that potentially contain anti-EF-1α antibodies which attach to the corresponding bound EF-1α antigen for detection purposes. The assay hereof has a sensitivity exceeding 86% and a specificity exceeding 89% for the detection of active SLE.

2. Description of the Prior Art

Rheumatological or rheumatic diseases are autoimmune disorders in which individuals characteristically produce antibodies against constituents of their own tissues. Systemic (non-organ specific) rheumatological diseases at least include SLE, scleroderma, rheumatoid arthritis, and Sjogren's syndrome. These diseases are particularly difficult to diagnose because the symptoms are nonspecific, e.g., general malaise and joint stiffness. In particular, due to this common symptomology, clinicians are often confronted with great difficulty in distinguishing between SLE and rheumatoid arthritis.

The difficulty of diagnosing rheumatological diseases is compounded due to the variance of symptomology between different SLE patients. SLE is currently diagnosed on the basis of eleven criteria that were established in 1982 by the American Rheumatism Association, and published as Tan, E. M. et al., 25 *Arthritis and Rheumatism* 1271 (1982). Patients who exhibit at least four of these criteria are diagnosed with SLE; however, only certain percentages of patients exhibit the respective symptoms. These symptoms and the percentage of patients exhibiting them include: malar rash (57%); discoid rash (18%); photosensitivity (43%); oral ulcers (27%); arthritis (86%); serositis including pleuritis (52%) or pericarditis (18%); renal disorders including proteinuria (50%) or urinary casts (36%); neurologic disorders including seizures (12%) or psychosis (13%); hematologic disorders including hemolytic anemia (18%), leukopenia (46%), or thrombocytopenia (21%); immunologic disorders including LE-cells (73%), anti-dsDNA (67%), anti-Sm (31%), or a false-positive test for syphilis (15%); and antinuclear antibody (99%).

Even after the initial diagnosis of SLE, the disease proceeds intermittently between periods of activity and inactivity, and during these periods the symptomology may vary widely. No single test is available for accurately determining the relative severity of the SLE disease over time. Most treating physicians rely upon a combination of tests and observations such as the Lupus Activity Criteria Count ("LACC"), which is published as Urowitz et al., 11 *J. Rheumatol* 783 (1983). A LACC score of +2 or greater is indicative of "active" SLE, while a score of less than +2 indicates an "inactive" SLE state. The LACC score criteria include: arthritis; abnormal blood tests including fewer than 4000 white blood cells per milliliter, CH50 (serum complement) values of less than 150, an anti-dsDNA antibody titer of 450 or greater; topical problems including a new rash, hair loss, or oral ulcers; pericarditis; central nervous system involvement including seizures or psychosis; vasculitis; or a urine test having greater than five red blood cells per milliliter.

While no cure for SLE is known at the present time, treatment options primarily include a general suppression of the immune system with drugs such as prednisolone, azathioprine, and cyclophosphamide, under the supervision of a physician. Each of these drugs produces undesirable side-effects in the patient, so it is beneficial to minimize the dosage whenever possible. During periods of SLE remission, it is possible to discontinue administration of these prescription drugs; however, drug therapy must be resumed at the first sign of relapse, in order to avoid potentially devastating complications. The ongoing process for monitoring the progression of SLE between periods of remission and relapse requires the patients to visit a clinic for multiple laboratory tests and examination by the physician. This constant need for testing and reevaluation significantly increases the cost of treating the disease.

A number of patents disclose methods for detecting anti-DNA antibodies and antibodies to extractable nuclear antigens in the sera of SLE patients. In U.S. Pat. No. 4,234,563, the method steps utilize the fluorescent second antibody technique to identify anti-DNA antibodies that bind with antigens including DNA-methylated bovine serum albumin conjugates or thymic extracts. U.S. Pat. No. 3,897,212 discloses a method for detecting anti-DNA antibodies in the serum of SLE patients, in which a patient's serum sample is incubated with radioactively labeled DNA for determining the amount of anti-DNA antibody in the serum.

U.S. Pat. No. 4,582,793 discloses a method for differentiating between various rheumatological diseases based upon the detection of anti-RNA polymerase I antibodies.

SUMMARY OF THE INVENTION

The present invention overcomes the problems discussed above, and provides an assay and materials which may be utilized for the selective diagnosis and monitoring of rheumatological diseases such as active SLE. The assay operates to detect specific antibodies in the body fluids of patients suffering from these diseases, and provides a very high degree of sensitivity and selectivity as compared to conventional diagnostic assays. The assay also provides a cost effective, non-invasive test that yields timely information about the level of disease activity in a particular patient. This timely information may be followed by an improved level of physician-directed changes in a course of prescribed medication for treating the disease.

It has been discovered that, unlike other persons, SLE patients produce a specific antibody to a common protein. All eucaryotic cells contain elongation factor 1-α ("EF-1α"), which is an enzyme that catalyzes the GTP-dependent binding of aminoacyl-tRNA to ribosomes in the process of translating mRNA into protein. This enzyme has been purified from various eucaryotic sources ranging from yeast to human (SEQID NO. 1) and, depending upon the cells of origin, consists of a single polypeptide chain having a $M_r$ of from about 48 to 53 kDa. Procaryotic cells have a highly homologous counterpart to EF-1α, which is referred to as EF-Tu and has a $M_r$ of about 43 kDa. The EF-1α amino acid residue sequence is highly conserved between human and other mammalian forms. There is even a high degree of conservation between human EF-1α and that from microorganisms including EF-1α or EF-Tu from procaryotic and eucaryotic cells. Therefore, while the respective EF-1α and EF-Tu proteins may have slightly different sequences, they can be considered as a highly conserved family of functional EF-1α homologues for purposes of the present assay. SLE patients, unlike normally healthy persons or even the majority of persons with other autoimmune diseases, produce antibodies that selectively attach to epitopes of the EF-1α family.

The invention pertains to an assay kit and method for detection and monitoring rheumatological disease by identifying anti-EF-1α antibodies in a body fluid taken from a patient. The assay method includes the steps of reacting anti-EF-1α antibodies in the fluid with substantially pure EF-1α based epitopes, and detecting the resultant antigen/antibody complex.

Most preferably, a quantity of substantially purified EF-1α enzyme is bound to a solid support for later use. The term "substantially purified" refers to a protein fraction that is essentially EF-1α, i.e., EF-1α constitutes at least 70% and more preferably at least about 85% of the protein content. In the past, EF-1α containing samples have included significant amounts of poly(A) polymerase ("PAP"), which is very similar in molecular weight and chromatographic properties to EF-1α. Care should be taken to avoid PAP contamination of EF-1α by proper purification techniques. The substantially purified EF-1α is preferably mixed in an aqueous buffer, and incubated in the presence of a solid support having protein binding sites, such as a polystyrene solid support.

The solid support bound enzyme is utilized as an antigen that reacts with anti-EF-1α antibodies when the support/enzyme complex is incubated in the presence of a body fluid sample containing anti-EF-1α antibodies. A support/antigen/antibody complex results, and the bound antibody is detected by means of a suitable indicator which binds with the antibody. Unbound portions of the EF-1α enzyme, the fluid sample, and the indicator reagent are removed at appropriate times by washing the support. The presence of bound indicator, if any remains present after the final washing, indicates the presence of bound antibody.

The body fluid is most preferably gathered as a urine sample and diluted for incubation with the bound EF-1α antigen. Alternatively, the fluid may comprise body fluids other than urine, such as saliva, cerebrospinal fluid, whole blood, blood plasma, or blood serum.

The support may be comprised of any chromatographic, bilbous, porous, capillary, or other material that may be used to immobilize proteins or polypeptides. The support is most preferably polystyrene, and the polystyrene may be in several forms, e.g., in bead form which is placed within diluted bodily fluid or formed as a microtiter well into which diluted bodily fluid is placed.

The EF-1α is preferably substantially pure, and is most preferably human EF-1α; however, logistical difficulties may exist in obtaining sufficient quantities of the purified human enzyme. Accordingly, EF-1α may also preferably be obtained from rat Morris hepatoma 3924A (a rat tumor available by this designation from the University of Kansas Department of Biochemistry in Lawrence, Kans.). Any alternative source of purified EF-1α, including recombinantly-derived clones incorporating the known genetic sequence, may be also used.

Those skilled in the art will understand that indicator reagents may be produced, according to conventional laboratory procedures, by attaching a suitable label to proteins that bind with antibodies. Antibody, in particular anti-EF-1α bound to support/EF-1α, may be detected by utilizing the indicator reagent in any conventional fluorescent, luminescent, radiometric, or colorimetric indicator technique. Suitable labels include chromogens, catalysts, fluorescent compounds, chemiluminescent compounds, radioactive molecules, colloidal particles, dye molecules, enzymes, enzyme substrates, latex particles, liposomes, and other compounds that are capable of producing indicator signals. The antibody-binding proteins include, for example, protein A, protein G, or secondary antibodies that are typically antibodies prepared from rabbits or goats to be reactive against human antibodies.

The indicator reagent may be detected or quantified by any appropriate technique corresponding to the type of indicating reagent that is utilized, e.g., a radiometric reagent may be detected in a gamma counter. The amount of indicator that is detected in the assay is proportional to the amount of anti-EF-1α antibody that is bound to the immobilized EF-1α, and is also proportional to the concentration of anti-EF-1α antibody in the fluid sample.

The anti-EF-1α antibody assay may be utilized to detect rheumatic disease and to differentiate between SLE and rheumatoid arthritis. Detection of anti-EF-1α antibodies indicates rheumatic disease, and more specifically SLE instead of rheumatoid arthritis.

The anti-EF-1α antibody assay may also be conducted at sequential times, in a process of treating patients who have SLE. The process includes the steps of conducting a first anti-EF-1α antibody assay on a first body fluid sample taken from a patient at a first time to quantify a first antibody concentration in the first body fluid sample, performing a second anti-EF-1α assay on a second body fluid sample taken from the patient at a second time to quantify a second antibody concentration; assessing a change in degree of severity in the disease by comparing the first and second concentrations; and administering a medicament in an effective amount for treating the disease according to the change in degree of severity.

Preferred forms of the invention include an assay kit having a support providing a quantity of substantially pure protein from the EF-1α family bound to the support, where the protein has a capacity for functioning as an antigen for the anti-EF-1α antibody that may be found in the body fluids of a patient. These assay kits may optionally include an appropriate indicator reagent, buffers, washing solutions, preservative agents, and stabilizing solutions.

Alternative assay kits may employ a competitive assay format, wherein suitably labeled anti-EF-1α antibodies are incubated with the support-immobilized EF-1α antigen in the presence of the body fluid test sample. The labeled antibodies compete with the anti-EF-1α antibodies that are naturally present in the fluid sample for attachment to the bound EF-1α. In this format, the quantity of label detected corresponds to the quantity of labeled anti-EF-1α bound to the immobilized antigen, and this quantity is inversely proportional to the amount of anti-EF-1α antibody that the test sample contains. The labeled anti-EF-1α antibodies may be produced according to protocols that are well known to those who are skilled in the art.

Another competitive assay format substitutes anti-EF-1α antibodies that are bound to the support instead of the EF-1α antigen. In this format, the EF-1α antigen is labeled to serve as the indicator reagent, and incubated with the bound antibody in the presence of the bodily fluid sample. The antibodies in the bodily fluid compete with the immobilized antibodies for attachment to the labeled EF-1α. Thus, in this format, the quantity of label detected corresponds to the amount of labeled EF-1α bound to immobilized anti-EF-1α, and is inversely proportional to the quantity of anti-EF-1α that is contained in the bodily fluid sample.

DETAILED DESCRIPTION OF THE PREFERRED EMBODIMENT

Preferred assays according to the invention may be performed according to the following non-limiting examples.

EXAMPLE 1

Immobilization of EF-1α on a Polystyrene Substrate

EF-1α (SEQID NO. 1) was purified from Morris hepatoma 3924A (a rat tumor available by this designation from the University of Kansas Department of Biochemistry in Lawrence, Kans.). The purification process applied conventional protocols for EF-1α purification such as those described by El-Hodiri, *Rat Hepatoma Poly(A) Polymerase: Partial Amino Acid Sequence and Incorporation into an Accurate in vitro Polyadenylation System* (University of Kansas Department of Biochemistry, Ph.D. ,Thesis, 1991), which is hereby incorporated by reference herein. While these purification techniques are generally known to those skilled in the art, pages 12–16 of the El-Hodiri reference discuss the purification techniques that are utilized in the copurification of poly(A) polymerase and EF-1α.

Hepatomas (Morris 3924a) were harvested from rats and necrotic tissue was removed. The hepatomas were rinsed with cold 0.9% NaCl containing 0.25M sucrose and minced. Minced tumor tissue was homogenized in 2M sucrose (54.4% (w/v); refractive index 1.43), 3.3 mM $MgCl_2$, 0.2 mM spermine, by four strokes at high speed in a Kontes homogenizer with a Teflon pestle, in 20 g portions, each in 180 ml of sucrose solution. The homogenate was brought up to 12 times the tumor weight with the sucrose solution and nuclei were pelleted by centrifugation (60 minutes at 39,000 x g; 18 krpm in a Sorvall SS-34 rotor) and the supernatant was discarded. Centrifuge tubes were drained on papers towels and their walls were wiped with Kimwipes to remove remaining cellular debris. To remove cytoplasmic contaminants, nuclei were resuspended in 0.34M sucrose (nuclease free), 1 mM $MgCl_2$, 0.3% Triton X-100 (1 ml per g of tumor) and pelleted by centrifugation (10 minutes at 5900 x g; 7 krpm in Sorvall SS-34 rotor). Nuclei were then resuspended in sonication buffer [50 mM Tris-HCl (pH 8.9), 50 mM KCl, 0.1 mM EDTA, 1 mM $MgCl_2$, 40% glycerol, 0.5 mM DTT, 0.5 mM PMSF] and disrupted by sonication (15 second bursts at high power until >90% of the nuclei were disrupted, typically 2 minutes total sonication time). The resulting solution was diluted with an 1.5 X volumes of dilution buffer (same as sonication buffer but without glycerol) and nuclear proteins were precipitated by addition of $(NH_4)_2SO_4$ (0.42 g per ml of solution). After centrifugation (1 hour at 100,000 x g; 30 krpm in Beckman Type 35 rotor), the nuclear pellet was resuspended in $TG_{25}MED$ (1.5 ml per g of tumor) and dialyzed overnight against $TG_{25}MED$ [50 mM Tris-HCl (pH 7.9), 25% glycerol, 5 mM $MgCl_2$, 0.1 mM EDTA, 0.5 mM DTT] (2×4 l, with one change for up to 400 g of tumor). Insoluble matter was removed from the dialysate by centrifugation (1 hour at 39,000 x g; 18 krpm in an SS-34 rotor) and the supernatant fraction (crude nuclear extract) was subjected to further purification steps.

The crude nuclear extract was applied to a DEAE Sephadex A25 column (1.7 ml per g of tumor) equilibrated with $TG_{25}M$ ED containing 10 mM $(NH_4)_2SO_4$. The column was washed with 1 bed volume of the same buffer and the effluent was pooled with the flow-through (DEAE-nPAP). This material was applied to a QAE Sephadex column (0.6 ml per g of tumor) equilibrated with $TG_{25}MED$ containing 10 mM $(NH_4)_2SO_4$. The flow-through was collected and the column was washed with 1.5 bed volumes of the same buffer. The flow through and wash were pooled (QAE-nPAP) and dialyzed overnight against $PG_{30}D$ (2×4 l, with one change for up to 400 g of tumor).

Dialyzed QAE-nPAP was applied to a phosphocellulose (PC) column (0.6 ml per g of tumor) equilibrated with $PG_{30}D$ containing 10 mM KCl. The column was washed with 1.5 bed volumes of the same buffer and bound proteins were eluted with a continuous linear gradient of 10 mM to 0.5M KCl in $PG_{30}D$ (4 bed volumes of each salt solution). Eighty fractions were collected and alternating fractions were assayed for PAP activity. Fractions with peak PAP activity were pooled (PC-nPAP) and dialyzed overnight against $PG_{30}D$ (4 l for up to 400 g of tumor).

Dialyzed PC-nPAP was applied to a hydroxylapatite (HA) column (0.14 ml per g of tumor) equilibrated with $PG_{30}D$ containing 10 mM KCl. The column was washed with 2.5 bed volumes of the same buffer and developed with a continuous linear gradient of 10 mM to 1M KCl in $PG_{30}D$ (2.5 bed volumes of each salt solution). Eighty fractions were collected and alternating fractions were assayed for PAP activity. Fractions containing peak PAP activity were pooled (HA-nPAP) and dialyzed overnight against 2 l $TG_{30}D$.

Dialyzed HA-nPAP was applied to a QAE-Sephadex A25 column (0.1 ml per g of tumor) equilibrated with $TG_{30}D$ containing 10 mM NaCl. The flow through and wash (2 bed volumes of equilibration buffer) were applied to a DNA-cellulose column (0.05 ml per g of tumor) equilibrated with $TG_{30}D$ containing 10 mM NaCl.

EF-1α activity was assayed in a mixture containing 24 mM HEPES-KOH (pH 7.6), 2.4 mM DTT, 0.1 mM spermine, 110 mM KOAc, 5 mM $Mg(OAc)_2$, 0.5 mM ATP (potassium salt), 0.1 mM GTP, 7.8 mM creatine kinase, 3 µg creatine phosphokinase, 0.6 $A_{260}$ units twice-washed wheat germ ribosomes, 60 pmol [$^{14}C$]-Phe-tRNA, and 0.2 µg wheat germ EF-2 in a total volume of 100 µl. (Wheat germ ribosomes and EF-2 were a generous gift of J. Ravel, University of Texas-Austin.) After 10 minutes incubation at 27° C., 1 ml 5% TCA was added and the mixture was heated for 10 minutes at 90° C. An additional 1 ml portion of 5% TCA was added to the mixture and the contents of the tube were filtered through a glass fiber filter (GF/C) using a vacuum manifold. Each tube was washed with 2 ml portions of 1% TCA, which were also filtered through the GF/C filters. Filters were dried for 10 minutes in a 100° C. oven and introduced into plastic scintillation vials. Three mls of scintillation fluid were added and radioactivity was measured in a scintillation counter. One unit of EF-1α activity is defined as that amount which will support the incorporation of 1 nmol of phenylalanine into polyphenylalanine under these conditions. In view of the similar natures of nuclear poly(A) polymerase and EF-1α, care was taken to utilize a shallow salt gradient ranging between about 0.01–0.30M NaCl for separation of EF-1α from poly(A) polymerase on the DNA-cellulose column followed by dialysis of the EF-1α fraction as the final step in purification.

A portion of purified EF-1α was immobilized on a polystyrene support. An aqueous phosphate buffer solution (pH 7.5) was prepared to include 25 mM potassium phosphate, 150 mM NaCl, 0.01% (w/v) sodium azide, and 0.1 mM phenylmethylsulfonylfluoride ("phosphate buffer"). The purified enzyme was diluted to a concentration of 6 μg/ml with the phosphate buffer, and placed in 600 nanogram portions into polystyrene microtiter wells (400 μl capacity, flat bottom, polystyrene Immulon I wells from Dynatech Laboratories, Inc., Alexandria, Va.). The wells containing the diluted enzyme solution were incubated for three hours at 37° C., to immobilize the enzyme at polystyrene protein binding sites. After incubation, the solution was removed and the wells were each washed four times with 0.1 ml of phosphate buffer.

A mixture was prepared to include phosphate buffer solution mixed with 1% (w/v) bovine serum albumin. This mixture was placed into each washed well in an amount of 0.15 ml/well, and incubated for one hour at room temperature to saturate any remaining protein binding sites of the polystyrene. The mixture was then removed to yield polystyrene microtiter wells having bound EF-1α.

EXAMPLE 2

Assay for the Detection of Anti-EF-1α Antibodies

The microtiter wells that were obtained from Example 1 were utilized in an assay for anti-EF-1α antibodies. For this assay, a Tris buffer (pH 7.4) was prepared to include 50 mM Tris-HCl, 150 mM NaCl, 5 mM ethylenediaminetetraacetic acid, 0.05% (v/v) Nonidet P-40 (purchased from Sigma Chemical of St. Louis, Mo.), and 0.1 mM phenylmethylsulfonylfluoride ("Tris buffer"). Human urine samples were obtained from SLE patients and healthy individuals and diluted in Tris buffer to a ratio of 1:10 (urine:buffer). A 0.1 ml portion of each diluted urine solution was placed in a separate microtiter well from Example 1. The wells containing the diluted urine were incubated for one hour at room temperature and then for sixteen hours at 4° C., in order to allow anti-EF-1α antibodies in the urine to bind with the immobilized EF-1α enzyme portion in each well. The diluted urine portions were removed from the wells, and the wells were then each washed four times with a 0.1 ml quantity of Tris buffer to remove unbound urine substituents.

The bound antibodies were tagged with a radioactive indicator. The Tris buffer was mixed to include radioactively-labeled ($^{125}$I) protein G. This protein G was purchased from Sigma Chemical of St. Louis, Mo., and radiolabelled, according to standard techniques, with $^{125}$I in an amount including $2\times10^{-4}$ mCi/ml (or 10–50 mCi/mg) as an antibody indicator reagent. This indicator reagent was added to the wells in a 0.1 ml/well amount, and the wells were incubated at room temperature for two hours while the radio-labeled protein G attached to the bound antibodies. After incubation, the reagent was removed and the wells were washed four times with a buffer solution (pH 7.4) containing 50 mM Tris-HCl, 1M NaCl, 0.4% (w/v) N-laurylsarcosine, and 0.1 mM phenylmethylsulfonylfluoride.

The washed wells containing indicator reagent bound to the test sample anti-EF-1α antibody which bound to EF-1α immobilized on the polystyrene wells, were analyzed in a gamma counter (Model 5110 from Packard of Meriden, Conn.) to yield a mean reading of 1828 cpm with SLE patients' urine (n=14) concomitant with a mean background count of 255 cpm with healthy individuals' urine (n=20) thus indicating the presence of anti-EF-1α antibodies in the SLE patents' urine samples.

EXAMPLE 3

Relationship Between Anti-EF-1α Antibodies and Systematic Lupus Erythematosus ("SLE")

The assay described in Example 2 was used to study human blood serum and urine samples from a variety of individuals including normally healthy persons as well as persons affected with various autoimmune and nonautoimmune diseases. Table 1 (below) provides a summary of the results, which demonstrate that the presence of antibodies to EF-1α in the sera and urine of the test subjects studied is highly correlated with the specific instance of active SLE, but not with rheumatoid arthritis.

Blood serum samples were obtained from eight normally healthy persons, from seventeen persons having a rheumatic disease other than SLE (eleven with rheumatoid arthritis, two with scleroderma, and four with dermatomyositis/polymyositis), and thirty-nine SLE patients. Of the thirty-nine SLE patients, ten patients had active disease indicated by a LACC score of 2, thirteen had mildly active disease indicated by a LACC score of 1, and sixteen patients had inactive disease indicated by a LACC score of 0.

Urine samples were obtained from twenty normally healthy persons, from eighteen persons having a rheumatic disease other than SLE (fourteen with rheumatoid arthritis, two with scleroderma, and two with dermatomyositis/polymyositis), three persons having a nonrheumatic disease (one with diabetes, two with urinary tract infections), and sixty SLE patients. Of the sixty SLE patients, fourteen patients had active disease indicated by a LACC score of 2, twenty had mildly active disease indicated by a LACC score of 1, and twenty-six patients had inactive disease indicated by a LACC score of 0.

TABLE 1

DISEASE SPECIFIC COMPARISON ANTI-EF-1α ANTIBODIES IN SERUM AND URINE SAMPLES

| Samples | # Tested | Number (%) with anti-EF-1α antibodies |
|---|---|---|
| URINE | | |
| SLE, active disease (LACC 2) | 14 | 13 (93%) |
| SLE, mildly active (LACC 1) | 20 | 5 (25%) |
| SLE, inactive (LACC 0) | 26 | 0 (0%) |
| SLE, all | 60 | 18 (30%) |
| Rheumatoid Arthritis | 14 | 1 (7%) |
| Scleroderma | 2 | 1 (50%) |
| Dermatomyositis/Polymyositis | 2 | 0 |
| Diabetes | 1 | 0 |
| Urinary Tract Infection | 2 | 0 |
| Normal | 20 | 0 |
| BLOOD SERUM | | |
| SLE, active disease (LACC 2) | 2 | 8 (80%) |
| SLE, mildly active (LACC 1) | 13 | 4 (31%) |
| SLE, inactive (LACC 0) | 16 | 8 (50%) |
| SLE, all | 39 | 20 (51%) |
| Rheumatoid Arthritis | 11 | 0 (0%) |
| Scleroderma | 2 | 1 (50%) |
| Dermatomyositis/Polymyositis | 4 | 0 |
| Normal | 8 | 0 |

EXAMPLE 4

Comparison of the Anti-EF-1α Antibody Tests with Conventional Tests with Respect to Specificity and Sensitivity of Detection of Active SLE The anti-EF-1α antibody assay results of Example 3 (Table 1) were compared, through their sensitivity and specificity values, to conventional laboratory tests which are commonly utilized to assess SLE disease status. These conventional laboratory tests and the results considered indicative of active SLE disease included serum complement (CH50) values of less than 150, serum anti-dsDNA titers of 450 or greater, and hematuria with greater than five red blood cells per milliliter of urine.

Table 2 illustrates the comparison of specificity and sensitivity between the anti-EF-1α antibody assay and the conventional laboratory tests where:

Sensitivity (%)=100×[(True Positives)/(True Positives+ False Negatives)]; and

Specificity (%)=100×[(True Negatives)/True Negatives+ False Positives)].

By way of example, a positive test for urinary anti-EF-1α antibody accurately reflected active SLE, as defined by the LACC scoring system, 93% of the time and a negative test for urinary anti-EF-1α antibody accurately reflected inactive SLE, as defined by the LACC scoring system, 89% of the time. In comparison, a positive test for hematuria accurately reflected active SLE only 29% of the time even though a negative test for hematuria agreed with the LACC scoring system for inactive SLE in 96% of the cases. Significantly, the urinary anti-EF-1α antibody test had a much greater sensitivity than all other tests. The urinary anti-EF-1α antibody test also had a relatively high specificity value, exceeded only by the specificity of the hematuria test, which had the lowest sensitivity value. The combined specificity and sensitivity value (93%+89%=182) of the urinary anti-EF-1α assay was much greater than the combined value for each of the conventional tests (150, 123, and 125 for depleted complement, anti-DNA, and hematuria, respectively), even though, unlike the conventional tests, the anti-EF-1α assay is not included in the LACC scoring system and the results would therefore be skewed in favor of the conventional tests.

TABLE 2

COMPARISON OF TEST SENSITIVITY AND SPECIFICITY FOR ACTIVE SLE

| Test | Sensitivity | Specificity |
| --- | --- | --- |
| Urinary anti-EF-1α antibody | 93% | 89% |
| Serum anti-EF-1α antibody | 80% | 59% |
| Depleted serum complement | 86% | 74% |
| Serum anti-DNA | 43% | 80% |
| Hematuria | 29% | 96% |

EXAMPLE 5

Monitoring SLE Disease Activity over Time Through Anti-EF-1α Antibodies

Urine samples from three SLE patients were collected over several months and assayed for anti-EF-1α antibodies according to the assay of Example 2. The present Example includes a description of the assay results over time for each patient and the treatment options which could have been made possible by these timely results.

PATIENT 1

The initial assay detected a high level of urinary anti-EF-1α antibody, as indicated by a 4,768 cpm reading from the gamma detector, as compared to a background (no EF-1α in the test well) radiation count of about 180. The treating physician assessed only a mildly active disease (based on a slightly depleted serum complement value) by the conventional LACC scoring system.

Responsive to the conventional LACC results, the treating physician decreased the patient's prednisolone dosage from 25 to 10 mg/day. Within two months, the patient was very ill (having a LACC score greater than 2) with a drastically depleted serum complement level, an elevated serum anti-DNA antibody titer, proteinuria, hematuria, leukocyturia, and severe arthritis. This drastic increase in disease severity might possibly have been avoided by maintaining or even increasing the prednisolone dosage if the initial, relatively high anti-EF-1α antibody test results could have been heeded.

After observing the symptoms of increased severity, the physician increased the prednisolone dosage to 40 mg/day, and one month later the patient was classified as mildly active, with an LACC score of 1 due to slightly depleted serum complement. At this time, the urinary anti-EF-1α antibody value was 1,183 cpm, which is significantly lower than the initial 4,768 reading for this patient, but still indicative of quite active disease. The physician maintained the 40 mg/day prednisolone dosage in view of the continuing active level of disease.

PATIENT 2

The initial anti-EF-1α antibody assay produced a gamma reading of 299 cpm, which was not significantly greater than background radiation, as an indicator of inactive disease. The physician assigned a LACC score of 1, which indicated mildly active disease, due to an elevated serum anti-DNA antibody value. The patient was receiving no medication, and the physician did not initiate drug therapy based upon this assessment.

Two months after the initial antibody assay, the patient's condition essentially had not changed according to the LACC score. Specifically, the patient continued to have an elevated serum anti-DNA antibody level, and the conventional urine tests for hematuria, proteinuria, and leukocyturia continued to provide results within normal ranges. The physician prescribed prednisolone at a relatively low dosage of 10 mg/day, due to the continued elevation of serum anti-DNA antibody. However, at this time, a second urinary anti-EF-1α antibody assay produced a 2,200 cpm gamma reading, which indicated a high level of disease activity.

Five months after beginning the course of prescribed medication, the urinary anti-EF-1α antibody assay produced a gamma reading of 4,639 cpm, which indicated a very severe level of disease activity; indeed, the patient was much worse, and had a LACC score greater than 2, which included elevated serum anti-DNA antibody, depleted serum complement, serositis, and proteinuria. These severe symptoms might have been avoided if the prednisolone dosage could have been increased as a precautionary measure based upon the 2,200 cpm assay five months prior, or even during the preceding or ensuing five months responsive to increasing urinary anti-EF-1α antibody.

PATIENT 3

The initial urine anti-EF-1α antibody assay produced a gamma reading of 247 cpm, which was not significantly greater than background, and indicated an inactive disease. Similarly, the physician assessed a LACC score of zero, which also indicated an inactive disease. The patient was taking 15 mg per day of prednisolone, and the physician began gradually reducing this already low dosage.

Four months after the initial assay, the patient was very ill, as indicated by a LACC score greater than two, with arthritis, serositis, depleted serum complement, elevated serum anti-DNA antibody, proteinuria, and hematuria. The urinary anti-EF-1α antibody assay produced a gamma reading of 2,222 cpm, which also indicated severely active disease.

The physician increased the prednisolone dosage due to the severe conventional symptoms. One month later, all of these symptoms had disappeared, except a slightly depleted serum complement, giving a LACC score of 1. At this time, the urinary anti-EF-1α antibody assay produced a gamma reading of 177 cpm (equivalent to normal background radiation), which indicated inactive disease.

---

I claim:

1. An assay kit for use in aiding in the detection of a rheumatological disease selected from the group consisting of SLE and scleroderma, comprising a solid support having a quantity of substantially purified enzyme from the EF-1α family bound to said support, said enzyme having a capacity for functioning as an antigen for anti-EF-1α antibody.

2. The kit as set forth in claim 1, said support including polystyrene having protein binding sites for attaching to said enzyme.

3. The kit as set forth in claim 1, including said enzyme selected from the group consisting of SEQID NO. 1 and purified functional homologues thereof.

4. The kit as set forth in claim 1, including said support forming at least a portion of a microtiter well plate.

5. The kit as set forth in claim 1, said substantially purified enzyme being at least about 70% pure.

6. A method aiding in the detection of a rheumatological disease selected from the group consisting of SLE and scleroderma, comprising the steps of:

obtaining a sample of body fluid from a patient, which may contain anti-EF-1α antibodies;

reacting said sample with an EF-1α antigen to produce an amount of antigen/antibody complex, if said sample contains said antibodies; and detecting said complexed antibody as an aid in the detection of rheumatological disease selected from the group consisting of SLE and scleroderma.

7. The method as set forth in claim 6, said step of obtaining a sample includes gathering a body fluid selected from the group consisting of urine, saliva, cerebrospinal fluid, whole blood, blood plasma, and blood serum.

8. The method as set forth in claim 7, said step of obtaining a sample includes gathering said body fluid selected from the group consisting of urine and blood serum.

9. The method as set forth in claim 7, said step of obtaining a sample incudes gathering urine.

10. The method as set forth in claim 6, said step of reacting includes applying said sample to microtiter wells having EF-1α antigen bound thereto.

11. The method as set forth in claim 10, said step of detecting includes reacting said wells with an indicator reagent for indicating the presence of bound antibody.

12. The method as set forth in claim 11, said step of detecting includes exposing said wells to an indicator reagent selected from a group consisting of fluorescent, luminescent, radioactive, and colorimetric reagents.

13. The method as set forth in claim 12, said step of exposing includes contacting said antibody with radioactively labeled protein G.

14. The method as set forth in claim 6, said step of detecting includes producing a radiation count reading indicative of the concentration of said complexed antibody.

15. The method as set forth in claim 6, said body fluid being urine, said rheumatological disease being active SLE, said method having a sensitivity for active SLE greater than about 86%.

16. The method as set forth in claim 15, said method having a sensitivity for said active SLE of at least about 90%.

17. The method as set forth in claim 15, said method having a specificity for said active SLE of at least about 89%.

18. The method as set forth in claim 6, in which detection of said complexed antibody specifically indicates active SLE and distinguishes active SLE and rheumatoid arthritis.

19. A method for directing treatment of a patient having systemic lupus erythematosus disease, comprising the steps of:

conducting a first anti-EF-1α antibody assay on a first body fluid sample taken from said patient at a first time, and quantifying a first antibody concentration in said first body fluid sample;

performing a second anti-EF-1α assay on a second body fluid sample taken from said patient at a second time and quantifying a second antibody concentration in said second body fluid sample;

comparing said first and second concentrations to assess a degree of change of severity in said disease; and administering a medicament in an effective amount for treating said disease according to said degree of severity.

20. The method as set forth in claim 19, said first assay comprising a radiometric assay.

21. The method as set forth in claim 19, said comparing step includes assessing active disease as an antibody concentration above a baseline level established for said patient.

22. The method as set forth in claim 19, said administering step includes reducing dosage of said medicament to a low maintenance level for treatment when said disease is inactive, and increasing dosage of said medicament to a disease-fighting level for treatment when said disease is active.

23. The method as set forth in claim 19, said administering step includes selecting prednisolone as said medicament.

24. The method as set forth in claim 19, said body fluid being selected from the group consisting of urine, saliva, whole blood, blood plasma, blood serum and cerebrospinal fluid.

25. The method as set forth in claim 24, said body fluid being urine.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 462 amino acids
        ( B ) TYPE: amino acid
        ( D ) TOPOLOGY: unknown ( i i ) MOLECULE TYPE: protein ( i i i ) HYPOTHETICAL: NO ( v i ) ORIGINAL SOURCE:
        ( A ) ORGANISM: Homo sapiens ( x ) PUBLICATION INFORMATION:
        ( A ) AUTHORS: Uetsuki,
        ( C ) JOURNAL: J. Biol. Chem.
        ( D ) VOLUME: 264
        ( F ) PAGES: 5791-5798
        ( G ) DATE: 1989
        ( K ) RELEVANT RESIDUES IN SEQ ID NO:1: FROM 1 TO 462

( x i ) SEQUENCE DESCRIPTION: SEQ ID NO:1:

```
Met Gly Lys Glu Lys Thr His Ile Asn Ile Val Val Ile Gly His Val
 1               5                  10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
               100                 105                 110

Val Leu Ile Val Ala Ala Gly Val Gly Glu Phe Glu Ala Gly Ile Ser
           115                 120                 125

Lys Asn Gly Gln Thr Arg Glu His Ala Leu Leu Ala Tyr Thr Leu Gly
       130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
               165                 170                 175
```

-continued

| | | | | | | | | | | | | | | |
|---|---|---|---|---|---|---|---|---|---|---|---|---|---|---|
| Tyr | Ile | Lys | Lys 180 | Ile | Gly | Tyr | Asn | Pro 185 | Asp | Thr | Val | Ala | Phe 190 | Val | Pro |
| Ile | Ser | Gly 195 | Trp | Asn | Gly | Asp | Asn 200 | Met | Leu | Glu | Pro | Ser 205 | Ala | Asn | Met |
| Pro | Trp 210 | Phe | Lys | Gly | Trp | Lys 215 | Val | Thr | Arg | Lys | Asp 220 | Gly | Asn | Ala | Ser |
| Gly 225 | Thr | Thr | Leu | Leu | Glu 230 | Ala | Leu | Asp | Cys | Ile 235 | Leu | Pro | Pro | Thr | Arg 240 |
| Pro | Thr | Asp | Lys | Pro 245 | Leu | Arg | Leu | Pro | Leu 250 | Gln | Asp | Val | Tyr | Lys 255 | Ile |
| Gly | Gly | Ile | Gly 260 | Thr | Val | Pro | Val | Gly 265 | Arg | Val | Glu | Thr | Gly 270 | Val | Leu |
| Lys | Pro | Gly 275 | Met | Val | Val | Thr | Phe 280 | Ala | Pro | Val | Asn | Val 285 | Thr | Thr | Glu |
| Val | Lys 290 | Ser | Val | Glu | Met | His 295 | His | Glu | Ala | Leu | Ser 300 | Glu | Ala | Leu | Pro |
| Gly 305 | Asp | Asn | Val | Gly | Phe 310 | Asn | Val | Lys | Asn | Val 315 | Ser | Val | Lys | Asp | Val 320 |
| Arg | Arg | Gly | Asn | Val 325 | Ala | Gly | Asp | Ser | Lys 330 | Asn | Asp | Pro | Pro | Met 335 | Glu |
| Ala | Ala | Gly | Phe 340 | Thr | Ala | Gln | Val | Ile 345 | Ile | Leu | Asn | His | Pro 350 | Gly | Gln |
| Ile | Ser | Ala 355 | Gly | Tyr | Ala | Pro | Val 360 | Leu | Asp | Cys | His | Thr 365 | Ala | His | Ile |
| Glx | Cys 370 | Lys | Phe | Ala | Glu | Leu 375 | Lys | Glu | Lys | Ile | Asp 380 | Arg | Arg | Ser | Gly |
| Lys 385 | Lys | Leu | Glu | Asp | Gly 390 | Pro | Lys | Phe | Leu | Lys 395 | Ser | Gly | Asp | Ala | Ala 400 |
| Ile | Val | Asp | Met | Val 405 | Pro | Gly | Lys | Pro | Met 410 | Cys | Val | Glu | Ser | Phe 415 | Ser |
| Asp | Tyr | Pro | Pro 420 | Leu | Gly | Arg | Phe | Ala 425 | Val | Arg | Asp | Met | Arg 430 | Gln | Thr |
| Val | Ala | Val 435 | Gly | Val | Ile | Lys | Ala 440 | Val | Asp | Lys | Lys | Ala 445 | Ala | Gly | Ala |
| Gly | Lys 450 | Val | Thr | Lys | Ser | Ala 455 | Gln | Lys | Ala | Gln | Lys 460 | Ala | Lys | — | |